US012594038B2

(12) United States Patent
Govari et al.

(10) Patent No.: US 12,594,038 B2
(45) Date of Patent: Apr. 7, 2026

(54) ESTIMATION OF CONTACT FORCE OF CATHETER EXPANDABLE ASSEMBLY

(71) Applicant: BIOSENSE WEBSTER (ISRAEL) LTD., Yokneam (IL)

(72) Inventors: Assaf Govari, Haifa (IL); Andres Claudio Altmann, Haifa (IL); Ilya Sitnitsky, Nahariya (IL); Alexander Shechtman, Haifa (IL); Amit Fuchs, Hogla (IL); Christopher Thomas Beeckler, Brea, CA (US); Joseph Thomas Keyes, Irvine, CA (US); Ishan Khan, Irvine, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 133 days.

(21) Appl. No.: 18/373,308

(22) Filed: Sep. 27, 2023

(65) Prior Publication Data

US 2025/0099041 A1     Mar. 27, 2025

(51) Int. Cl.
| | |
|---|---|
| *A61B 5/00* | (2006.01) |
| *A61B 5/06* | (2006.01) |
| *A61B 5/287* | (2021.01) |
| *A61B 5/367* | (2021.01) |
| *A61B 18/14* | (2006.01) |

(52) U.S. Cl.
CPC ............ *A61B 5/6885* (2013.01); *A61B 5/062* (2013.01); *A61B 5/287* (2021.01); *A61B 5/367* (2021.01); *A61B 5/6858* (2013.01); *A61B 18/1492* (2013.01)

(58) Field of Classification Search
CPC ....... A61B 5/6885; A61B 5/062; A61B 5/287; A61B 5/367; A61B 5/6858; A61B 18/1492; A61B 5/063; A61B 5/4836; A61B 2090/064; A61B 2090/065; A61B 2562/022; A61B 5/065; A61B 5/6843; A61B 5/6859; A61B 2034/2051
See application file for complete search history.

(56) References Cited

U.S. PATENT DOCUMENTS

| | | | |
|---|---|---|---|
| 5,391,199 A | 2/1995 | Ben Haim |
| 5,443,489 A | 8/1995 | Ben Haim |
| 5,558,091 A | 9/1996 | Acker |

(Continued)

OTHER PUBLICATIONS

Extended European Search Report received for European Application No. 24202736.5 mailed on Feb. 3, 2025, 8 pages.

*Primary Examiner* — Michael J Carey
*Assistant Examiner* — Zainab Mohammed Aldarraji

(57) ABSTRACT

A system includes a medical probe and a processor. The medical probe includes a shaft for insertion into a cavity of an organ of a patient; an expandable assembly fitted at a distal end of the shaft, wherein the expandable assembly has elastic properties; a position sensing element mounted on the distal end of the shaft; and at least one distal position sensing element on a distal end of the expandable assembly. The processor senses relative location of each of the at least one distal position sensing element and the proximal position sensing element; determines deflection of the expandable assembly based on the relative location; relates the deflection to the contact force applied on the expandable assembly; and provides an indication of the contact force on a display.

19 Claims, 4 Drawing Sheets

(56)  References Cited

U.S. PATENT DOCUMENTS

| | | | | |
|---|---|---|---|---|
| 6,172,499 | B1 | 1/2001 | Ashe | |
| 6,239,724 | B1 | 5/2001 | Doron | |
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben Haim | |
| 6,788,967 | B2 | 9/2004 | Ben Haim | |
| 6,892,091 | B1 | 5/2005 | Ben Haim | |
| 7,536,218 | B2 | 5/2009 | Govari | |
| 7,756,576 | B2 | 7/2010 | Levin | |
| 7,848,787 | B2 | 12/2010 | Osadchy | |
| 7,869,865 | B2 | 1/2011 | Govari | |
| 8,456,182 | B2 | 6/2013 | Bar-Tal | |
| 8,535,308 | B2 | 9/2013 | Govari | |
| 2004/0133091 | A1* | 7/2004 | Fuimaono | A61B 5/287 |
| | | | | 600/374 |
| 2009/0138007 | A1* | 5/2009 | Govari | A61B 5/065 |
| | | | | 606/33 |
| 2015/0342700 | A1 | 12/2015 | Govari et al. | |
| 2021/0128010 | A1* | 5/2021 | Govari | A61B 5/062 |
| 2023/0147259 | A1 | 5/2023 | Govari et al. | |
| 2024/0033008 | A1 | 2/2024 | Govari et al. | |
| 2024/0206978 | A1 | 6/2024 | Govari et al. | |

\* cited by examiner

402 — Insert expandable assembly into cavity

404 — Bring expandable assembly into contact with wall tissue of cavity

406 — Acquire location and/or orientation data using transmitter-receiver mode of EMCs 408 — Estimate amount of change of assembly shape and/or orientation relative to distal end of shaft 410 — Using elastic model and/or empirical data of cage elasticity, relate amount of change to contact force applied on the expandable assembly 412 — Provide indication of contact force on a display

*FIG. 4*

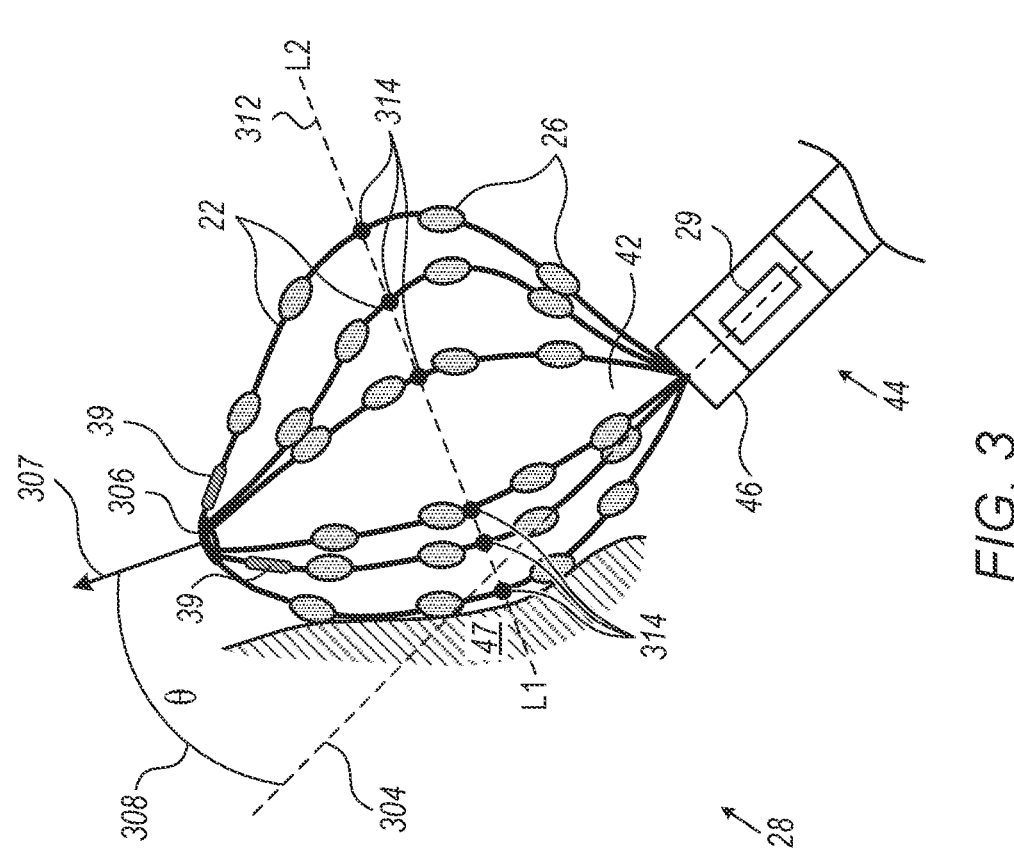

*FIG. 3*

ESTIMATION OF CONTACT FORCE OF CATHETER EXPANDABLE ASSEMBLY

FIELD OF THE DISCLOSURE

The present disclosure relates generally to invasive medical probes, and particularly to detection of contact force of cardiac catheters.

BACKGROUND OF THE DISCLOSURE

Cardiac catheters typically comprise an elongated shaft for insertion into the body of a patient and a distal end including one or more electrodes and/or sensors. The catheter may further comprise a magnetic position sensor fitted at the distal end of the shaft.

Using signals acquired by the magnetic location sensor, a processor can accurately estimate the position and orientation of the distal end of the shaft inside the body of the patient.

It is also known to sense contact force applied on the distal end. One way to estimate the contact force of the distal end assembly is described in U.S. Pat. No. 8,535,308. The patent describes a spring-loaded joint that couples the distal tip to the distal end of the shaft. A joint sensor, contained within the catheter senses a position of the distal tip relative to the distal end of the shaft. The joint sensor includes first and second subassemblies, which are disposed within the catheter on opposite, respective sides of the joint and each includes one or more magnetic transducers. The deflection is estimated from the relative locations of the subassemblies based on position signals they emit and receive. The tip contact force is estimated from the deflection based on the known spring constant of the joint.

The present disclosure will be more fully understood from the following detailed description of the examples thereof, taken together with the drawings, in which:

BRIEF DESCRIPTION OF THE DRAWINGS #

FIG. 3 is a schematic, pictorial illustration of a catheter expandable distal end assembly in a deformed shape while being pressed against tissue, in accordance with examples of the present disclosure; and FIG. 4 is a flow chart that schematically illustrates a method to estimate a contact force of an expandable distal end assembly, such as of FIG. 2 or 3, in contact with tissue, in accordance with an example of the present disclosure.

DETAILED DESCRIPTION OF EXAMPLES

Overview

Figure 1:
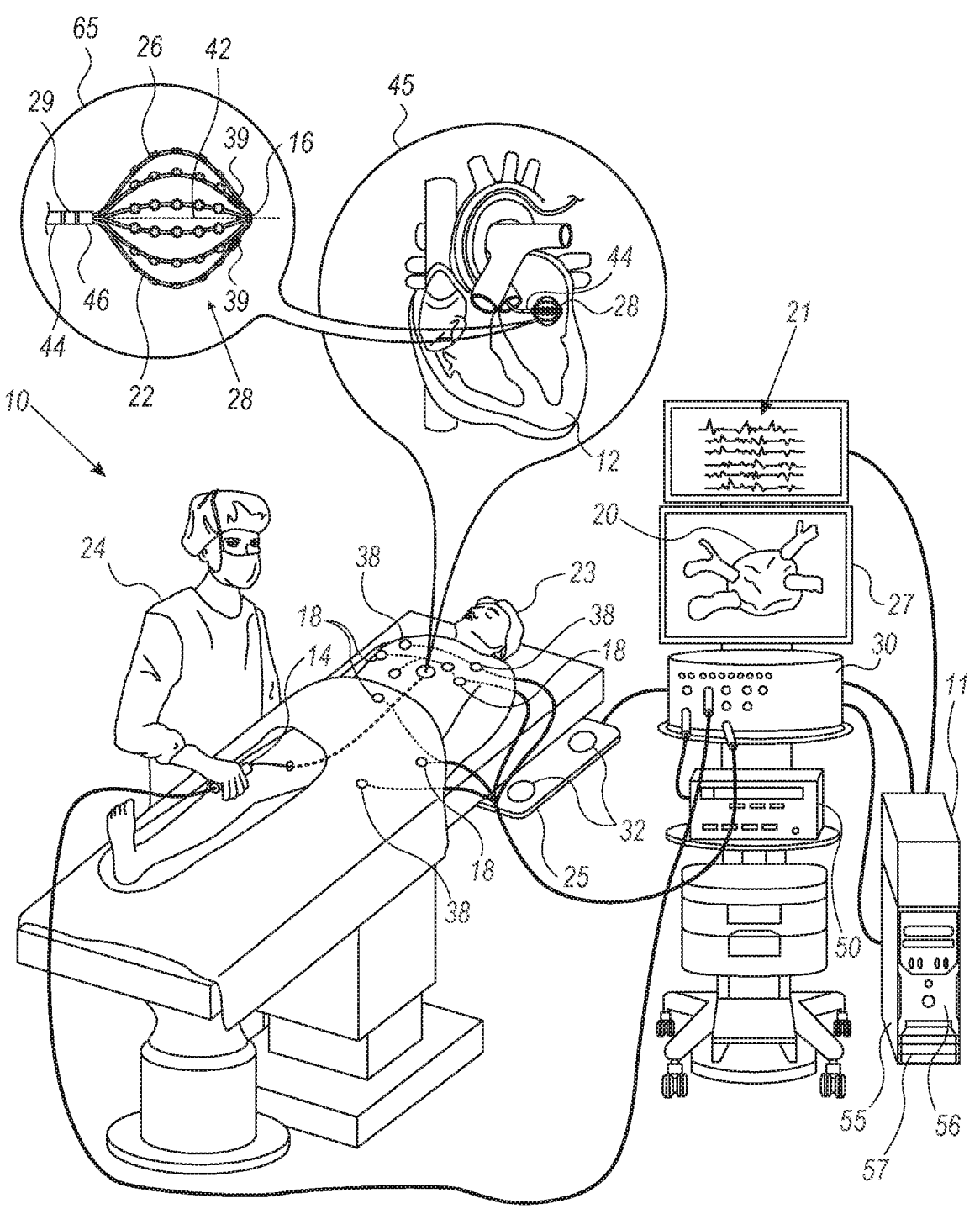
FIG. 1 is a schematic, pictorial illustration of a catheter-based electroanatomical (EA) mapping and ablation system, in accordance with an example of the present disclosure.

A wall cavity of an organ of a patient, such as a cardiac cavity, can be mapped and/or ablated using a catheter having multiple electrodes fitted at an expandable distal end assembly of the catheter. The expandable distal-end assembly is coupled at a distal end of a catheter shaft for insertion into the cavity. The expandable distal end assembly may be shaped in the form of a balloon, basket and/or another type of cage and may include a plurality of electrodes configured for sensing and/or delivering therapeutic signals. The expandable distal end assembly may comprise a plurality of splines connected at their proximal and distal ends. When expanded, the splines bow radially outwardly. When collapsed, the splines are arranged generally along the axis of the shaft. The electrodes and/or sensors may be arranged on the spline and/or on a membrane of a balloon, for a balloon distal end. The expandable distal-end assembly may also be referred to herein as the expandable assembly.

In a mapping and/or ablation procedure of a cardiac chamber, the physician expands the assembly and manipulates the expanded distal-end assembly for the electrodes to contact chamber walls. The quality of electroanatomical mapping (e.g., based on acquired depolarization signals by the electrodes) and/or ablation depends on the contact force of the electrodes with wall tissue. The estimation of such a force on the shaft may be difficult, as the elasticity of the expandable distal end assembly can cause contraction, tilt, and deformation of the expandable distal end assembly relative to a distal end of the shaft.

Therefore, when displaying visual indicia of the distal end assembly on an EA map in real-time, there may be a significant discrepancy between electrode locations as estimated based on the location and orientation of the magnetic sensor and actual locations of the electrodes. It is, however, clinically important to know the actual deflection of the distal end assembly and the contact force on the distal end assembly (e.g., to evaluate readiness for ablating tissue).

Examples of the present disclosure that are described herein provide a technique in which a processor estimates a contact force of an expandable distal-end assembly based on locally estimating a change in the expandable assembly's deflection. The disclosed technique involves sensing relative location of one or more first position sensing elements at the distal end and the at least second position sensing element at a distal end of the shaft (or a proximal end of the expandable distal-end assembly).

In some example embodiments, the one or more first position sensing elements at the distal end of the distal-end assembly and the at least one second position sensing elements at the distal end of the shaft, are electromagnetic coils (EMCs). Position sensing based on transmission between EMCs mounted on a catheter and EMCs embedded in a location pad are described in more detail herein.

In some example embodiments, the one or more first position sensing elements at the distal end of the distal-end assembly and the at least one second position sensing elements at the distal end of the shaft, are electrodes that sense position based on impedance tracking as described in more detail herein. Other position sensing elements (also referred to as position sensors) may be contemplated.

Using an elastic model of the expandable assembly and/or calibration, the processor estimates from the change of shape and/or deflection, the amount of force exerted on tissue by the expandable distal end assembly.

In some example embodiments, the relative location of is defined based on determining location of each position sensor (or electrode) within a defined a global coordinate system and determining a relative location. In other example embodiments, the relative location of each position sensor is based on measuring one or more location signals acquired in a local transmitter-receiver mode that does not require first determining location of each position sensor (or electrode) within a defined a global coordinate system. Using the local signals, the processor calculates the relative position of a transmitting element to a receiving element where one of them is on the shaft and the other is on the expandable assembly.

In some example embodiments, the processor uses the local transmitter-receiver mode by using proximal and distal EMCs, where the distal EMCs are disposed on a distal portion of the expandable assembly and the proximal EMC is disposed on a distal end of the shaft. Typically, three distal EMCs may be used.

In the local transmitter-receiver mode, one EMC group (e.g., the distal EMC(s)) emits magnetic fields, and the other EMC (the proximal EMC(s)) outputs electrical signals in response to picking up the magnetic fields. This local transmitter-receiver mode may yield a more accurate estimation of deflection and of changes in the shape of the expandable distal end assembly as compared to methods that require first determining each position of each position sensor within a global coordinate system.

Depending on the number of distal EMCs and/or their distribution over the expandable distal end assembly, the disclosed technique can provide an accurate estimation of the contact force of the expandable distal end assembly. For example, the processor can estimate where the contact occurs over a lateral circumference of the expandable distal end assembly by detecting a tilt direction of the expandable distal end assembly. By detecting a deformation, the processor can estimate the location of an epicenter of the contact on the lateral circumference (e.g., whether the location is on a portion closer to the shaft or at a more distal portion of the expandable distal end assembly).

In one example, based on the magnetic fields generated by the distal EMC and sensed by the proximal EMC, a processor determines the distance and angle between the two EMCs and converts changes in distance and angle values from free space values to contact force exerted on the assembly.

The expandable distal end assembly is typically made of Nitinol or some other material that has elastic properties. Each of the splines of the expandable distal end assembly is an elastic beam and as the splines are all connected at their proximal and distal ends, the expandable distal end assembly can be elastically modeled as a structure made of elastic beams. The processor can therefore deduce a force applied on the expandable distal end assembly as an elastic element. When a simple spring model for expandable distal end assembly contraction and tilt is too limited (e.g., for some types of expandable distal end assemblies), the processor may use a more complex elastic model (e.g., based on a set of springs or beams) for the expandable distal end assembly deformation. One example of a system and method for tracking coordinates of elements (e.g., spline portion, sensors, electrodes) of an expandable distal end assembly in contact with tissue is described in U.S. patent application Publication Ser. No. 17/874,224 filed on Jul. 26, 2022. Another example of such a system and method for tracking coordinates of elements is described in U.S. patent application Publication Ser. No. 18/089,428 filed on Dec. 27, 2022. A processor using these techniques can find the location of electrodes under the deformed shape of the expandable distal end assembly.

Additionally, or alternatively, the processor can estimate the contact force using empirical data comprising calibration of the forces against expandable distal end assembly deformations. The processor may use weights to interpolate between calibration values. In such a case, a memory of the system is configured to store a relationship between EMC output and contact force based on the empirical data (e.g., a look-up table). The processor is configured to use the stored empirical data to relate EMC output to contact force.

In another example, the force on each spline (or each electrode) can be estimated based on modeling the shape of the expandable distal end assembly for different calculated forces. The modeled forces on the splines can be compared to pre-measured values, and the comparison can then be used to calibrate the model with weights. (Such weights can also be of a neural network model.)

In one example, the distal EMC is a magnetic single-axial sensor (SAS) configured to generate at least one respective oscillating magnetic field signal. The distal end of the shaft comprises a magnetic tri-axial sensor (TAS) made of three mutually orthogonal EMCs, the TAS configured to output electrical signals in response to magnetic field signal reception. In another example, the distal end of the shaft comprises three EMCs that are parallel and displaced for one another on the shaft.

The distal EMC is configured to pick up magnetic fields generated by a location pad, and the processor is configured to sample the resulting output and use it to determine a position of the distal coil in a 3D coordinate system. The TAS comprises three mutually orthogonal EMCs configured to pick up magnetic fields generated by a location pad, whereas the processor is configured to sample the resulting output and to use it to determine position and orientation of the shaft in a 3D coordinate system.

Any given frequency used for contact force detection is different from frequencies generated by an external location pad of a position-tracking system for position sensing.

In yet another example, the distal EMC (e.g., SAS) is embedded in a respective electrode disposed on a spline of the expandable distal end assembly.

System Description

FIG. 1 is a schematic, pictorial illustration of a catheter-based electroanatomical (EA) mapping and ablation system 10, in accordance with an example of the present disclosure.

System 10 includes one or more catheters, which are percutaneously inserted by physician 24 through the patient's vascular system into a chamber or vascular structure of a heart 12. Typically, a delivery sheath catheter is inserted into the left or right atrium near a desired location in heart 12. Thereafter, one or more catheters in turn can be inserted into the delivery sheath catheter to arrive at the desired location. The one or more catheters may include catheters dedicated for sensing intracardiac electrogram (IEGM) signals, catheters dedicated for ablating and/or catheters dedicated for both sensing and ablating. An example basket catheter 14 that is configured for sensing IEGM is illustrated herein. As seen in inset 45, physician 24 brings a basket type of expandable distal end assembly 28 (also called hereinafter "expandable distal-end assembly 28") fitted on a shaft 44 of catheter 14 into contact with the heart wall for sensing a target site in heart 12. For ablation, physician 24 similarly brings a distal end of an ablation catheter to a target site for ablating.

As seen in inset 65, catheter 14 is an exemplary catheter that includes one, and preferably multiple, electrodes 26 optionally distributed over a plurality of splines 22 at expandable distal-end assembly 28 and configured to sense IEGM signals. Catheter 14 additionally includes (i) a proximal position sensor 29 (e.g., TAS 29 comprising three EMCs) embedded in a distal end 46 of shaft 44 near expandable distal end assembly 28, and (ii) two distal position sensors 39 (e.g., SAS 39 comprising a single EMC)

to track the position of the distal end of expandable assembly 28. Optionally, and distal end preferably, position sensors 29 and 39 are magnetic-based position sensors that include magnetic coils for sensing three-dimensional (3D) position.

Figures 2A, 2B:
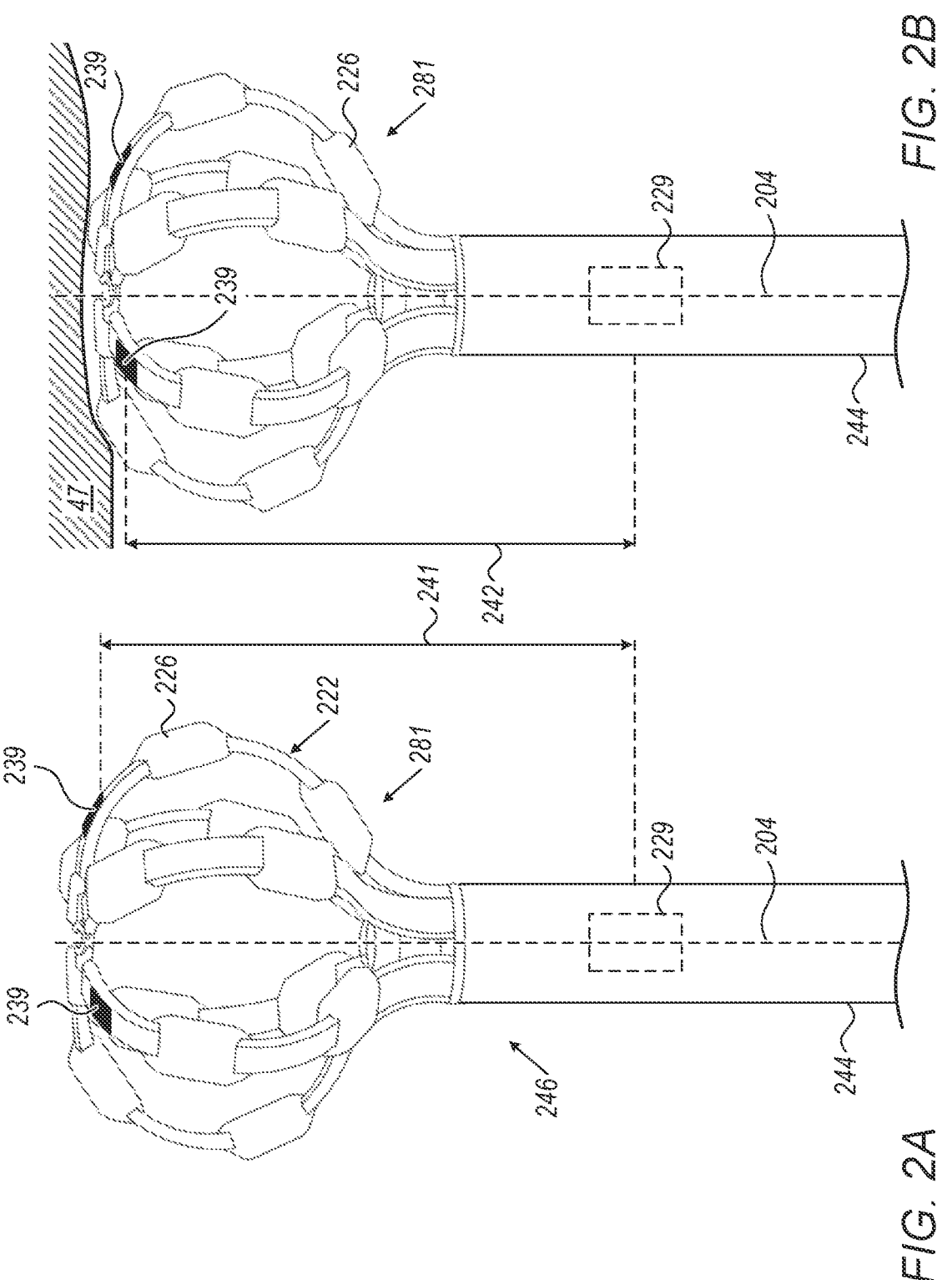
FIGS. 2A-2C are schematic, pictorial illustrations of a catheter expandable distal end assembly (i) in free space, (ii) compressed against tissue, and (iii) tilted by contacting tissue, respectively, in accordance with examples of the present disclosure.
Figure 2C:
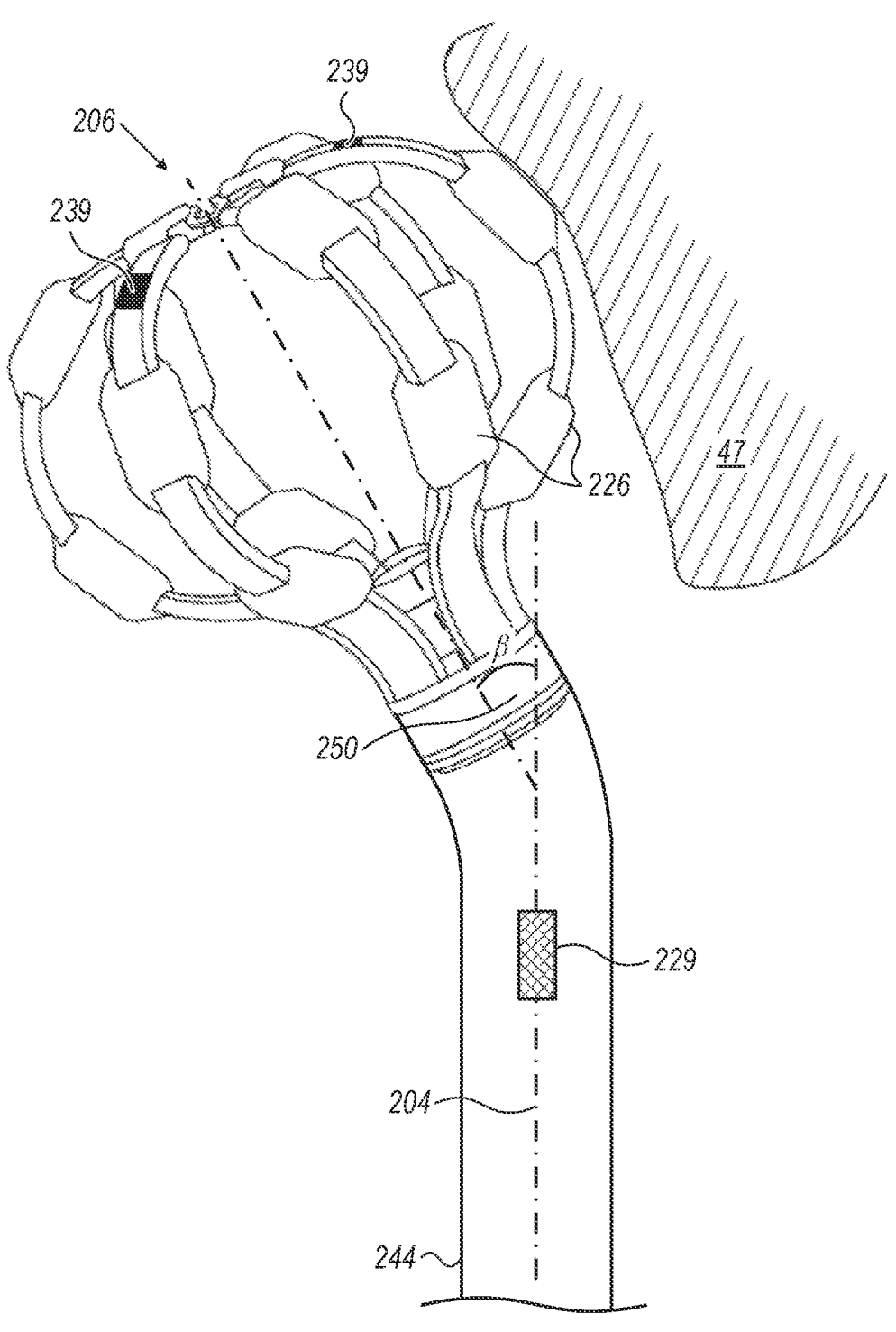

FIGS. 2B and 2C below show two scenarios where the EMCs of distal sensors 39 and proximal sensor 29 are used together for estimating the contact force of an elastic expandable distal end assembly with tissue. In FIG. 2B the force is estimated from expandable distal end assembly contraction relative to the distal end of the shaft, while in FIG. 2C the force is estimated from expandable distal end assembly tilt relative to the distal end of the shaft.

In the disclosed contact force estimation technique, the EMCs of distal and proximal sensors 39 and 29 are operated in a transmitter-receiver mode, with one EMC (e.g., of sensor 39) emitting magnetic fields, and the other EMC (e.g., of sensor 29) outputting electrical signals in response to receiving the magnetic fields. This transmitter-receiver mode, used by a processor to estimate contact force, yields more accurate location and orientation data than data yielded by using EMCs with a magnetic field source that is external to the patient's body.

Moreover, magnetic position sensors (29, 39) may also be operated together with an external location pad 25 that includes a plurality of magnetic coils 32 configured to generate magnetic fields in a predefined working volume. The frequencies of these fields are different from any given frequency used in the local transmitter-receiver mode for contact force detection, thus eliminating confusion between signals. Using the operation with external location pad 25 (at a different frequency for each EMC), the processor can determine the position of EMC 39 on a coordinate system of the position tracking system.

Real-time orientation of expandable distal end assembly 28 of catheter 14 can, in this way, be calculated from tracked locations of sensors 29 and 39 (locations being tracked using magnetic fields generated with location pad 25 and sensed by magnetic-based position sensors 29 and 39). This relative orientation is manifested by an angle formed between distal end 46 and a longitudinal axis 42 of expandable assembly 28 (to a distal edge 16 of the assembly). Distal end 46 of shaft 44 may comprise an amplifying circuit configured to amplify the output from the three EMCs of sensor 29.

Details of the magnetic-based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish a location reference for location pad as well as impedance-based tracking of electrodes 26. For impedance-based tracking, electrical current is directed toward electrodes 26 and sensed at electrode skin patches 38, such that the location of each electrode can be triangulated via electrode patches 38. Details of the impedance-based location tracking technology are described in U.S. Pat. Nos. 7,536,218; 7,756,576; 7,848, 787; 7,869,865; and 8,456,182.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses that may be used to effect irreversible electroporation (IRE), or combinations thereof.

Patient interface unit (PIU) 30 is a controller with processing capability that is configured to establish electrical communication between catheters, electrophysiological equipment, power supply and a workstation 55 for controlling the operation of system 10. Electrophysiological equipment of system 10 may include, for example, multiple catheters, location pad 25, body surface ECG electrodes 18, electrode patches 38, ablation energy generator 50, and recorder 11. Optionally, and preferably, PIU 30 additionally includes processing capability for implementing real-time computations of catheter locations and for performing ECG calculations.

Workstation 55 includes memory 57, processor unit 56 with memory or storage with appropriate operating software loaded therein, and user interface capability. Workstation 55 may provide multiple functions, optionally including (i) modeling endocardial anatomy in three-dimensions (3D) and rendering the model or anatomical map 20 for display on a display device 27, (ii) displaying on display device 27 activation sequences (or other data) compiled from recorded electrograms 21 in representative visual indicia or imagery superimposed on the rendered anatomical map 20, (iii) displaying real-time location and orientation of multiple catheters within the heart chamber, and (iv) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Estimation of Contact Force of Catheter Expandable Assembly

FIGS. 2A-2C are schematic, pictorial illustrations of a catheter expandable distal end assembly 281 (i) in free space, (ii) compressed against tissue 47, and (iii) tilted by contacting tissue 47, respectively, in accordance with examples of the present disclosure.

Expandable distal end assembly 281 is formed by spines 222 and comprises two distal EMCs 239, and a TAS 229 comprising three EMCs that are mutually orthogonal. In FIG. 2A expandable distal end assembly 281 is in free space and has a given first length 241. The transmitter-receiver layout 229/239 of FIG. 2 is only one of many more possible realizations of the disclosed transmitter-receiver configuration for contact force sensing. As another example, there can be three EMCs at the distal end of the catheter expandable distal end assembly while the shaft has only a dual-axis magnetic sensor (DAS).

In FIG. 2B, once pressed against tissue 47 (e.g., with some of electrodes 226 brought into firm contact with wall tissue), the elastic expandable distal end assembly 281 contracts into a second, shorter, length 242. Such a scenario may be typical in cases of pulmonary vein isolation (PVI) procedures, where some distal electrodes 226 are used in this way to electrically ablate an ostium of a PV in a left atrium to eliminate an arrhythmia.

The transmitter-receiver mode of the EMCs 239 and one of TAS 229 enables accurate determination of the amount of expandable distal end assembly contraction $D_L$ (e.g., length 241 minus length 242). Based on a known (e.g., measured) spring coefficient $K_L$ of expandable distal end assembly 281, a contact force $F_c$ can be estimated from $F_c = K_L \cdot D_L$.

In FIG. 2C, expandable distal end assembly 281 is brought to side contact with tissue 47. As a result, expandable distal end assembly 281 is tilted or bent from its zero-angle orientation (as seen in FIG. 2A) into an angle β 250 (an angle between a longitudinal axis 204 of the distal end of shaft 244 and an axis 206 of the expandable distal end assembly). Such a scenario may be typical in cases where some electrodes 226 are used for ablating wall tissue of a ventricle to eliminate a ventricular arrhythmia.

The transmitter-receiver mode of the EMCs 239 and these of TAS 229 enable accurate determination of the amount of expandable distal end assembly tilt β. Based on a known (e.g., measured) spring coefficient $K_A$ of expandable distal end assembly 281, measured or pre-known distance L between the EMCs 239 and EMCs of sensor 229, and L (e.g., length 241), a contact force FA can be estimated from $F_A=K_A·L·β$.

As noted above, when a simple spring model for expandable distal end assembly contraction and tilt is limited (e.g., for some types of expandable distal end assemblies), the processor may use a more complex elastic model (e.g., based on a set of springs) for expandable distal end assembly deformation, as seen in FIG. 3.

Additionally, or alternatively, the processor can estimate the contact force using empirical data comprising calibration of the forces against expandable distal end assembly tilt and/or deformation. The processor may use weights to interpolate between calibration values. In such a case, a memory of the system is configured to store a relationship between EMC output and contact force based on the empirical data. The processor is configured to use the stored empirical data to relate EMC output to contact force.

FIG. 3 is a schematic, pictorial illustration of the catheter expandable distal end assembly 28 in a deformed shape while being pressed against tissue 47, in accordance with examples of the present disclosure.

As seen, expandable distal end assembly 28 develops an angle θ 308 with respect to the distal end 46 of shaft 44. Angle 308 is defined between a longitudinal axis 307 of the expandable distal end assembly and a longitudinal axis 304 of distal end 46. Using EMCs 39, EMCs of TAS 29, and known relations between a distal edge 306 of the assembly and distal end 46, the processor can readily calculate angle Θ 308. The processor can calculate the amount of deflection of distal edge 306 based on the tilt angle and the length of the expandable distal end assembly (e.g., length 241).

Unknown, however, is the shape followed by splines 22, though it is evident that splines 22 on the pressed side (L1) are compressed inward, whereas splines 22 on the free side (e.g., in a cardiac chamber blood pool) are bowed outward. To estimate tilt, it is sufficient to know that sensors 39 move together with small relative change between their movement due to deformation, and this change can be largely considered. As a result, expandable distal end assembly deformation doesn't cause any significant error in the estimated contact force.

If smaller effects of deformation are of interest, the analysis of the deformed shape can be done using the aforementioned U.S. patent application Publication Ser. No. 18/089,428 by looking at a frontal cross-sectional plane L1-L2 312 (e.g., the azimuthal plane). Since splines 22 are elastic and continuous, the processor can reconstruct the entire expandable distal end assembly shape by finding spline locations 314 in one such plane.

Using a look-up table of measured contact forces against spline location values in plane L1-L2 312 (e.g., a look-up table stored in memory 57), processor 56 can estimate (e.g., interpolate) exceedingly accurately the actual contact force inside the patient's body.

A Method for Estimating Contact Force of Catheter Expandable Assembly

FIG. 4 is a flow chart that schematically illustrates a method to estimate a contact force of an expandable distal-end assembly, such as of FIG. 2 or 3 (e.g., basket expandable distal end assembly 28 or 281) in contact with tissue, in accordance with an example of the present disclosure. The algorithm, according to the presented example, carries out a process that begins with physician 24 inserting the expandable distal-end assembly into a cavity (e.g., a cardiac chamber), at expandable distal end assembly insertion step 402.

Next, at assembly contacting step 404, the physician brings the expandable distal end assembly into contact with the cavity wall tissue (e.g., tissue 47), which leads to the expandable distal end assembly changing shape or orientation relative to distal end of shaft, as seen in FIGS. 2B, 2C and 3.

At signal acquisition step 406, processor 56 receives location and/or orientation indicative signals acquired by EMCs (e.g., EMCs 39/239 or those of TAS 29/329) implemented in a local transmitter-receiver mode as described above.

Using the location and/or orientation indicative signals, the processor estimates an amount of change in shape and/or orientation of the expandable distal end assembly relative to the distal end of the shaft, in an assembly change estimation step 408.

Using an elastic model and/or empirical data (e.g., a look-up table stored in memory 57), processor 56 relates the amount of change to contact force applied on the expandable distal end assembly (e.g., to a basket type of cage), at contact force estimation step 410.

Finally, the processor provides an indication of the contact force (e.g., size and location over the expandable distal end assembly) to a user on a display, at contact force displaying step 412.

The flow chart shown in FIG. 4 is chosen purely for the sake of conceptual clarity. The present example may also comprise additional steps of the algorithm, such as estimating electrical conductivity between given electrodes and tissue. This and other possible steps are omitted from the disclosure herein purposely to provide a more simplified flow chart.

It is noted that although most of the examples have been described in reference to determining relative location using on a local transmitter-receiver mode, the system and method described herein may alternatively and/or additionally use position sensing of each position sensor (electrode) in reference to a global coordinate system to determine the relative locations.

EXAMPLES

Example 1

A system (10) includes a medical probe (14) and a processor (56). The medical probe (14) includes (i) a shaft (44) for insertion into a cavity of an organ of a patient (23), (ii) an expandable assembly (28) fitted at a distal end (46) of the shaft (44), wherein the expandable assembly (28) has elastic properties, (iii) a proximal position sensing element (29) mounted on the distal end (46) of the shaft, and (iv) at least one distal position sensing element (39) on a distal end of the expandable assembly (28). The processor (56) is configured to (I) sense relative location of each of the at least one distal position sensing element (39) and the proximal position sensing element (29), (II) determine deflection of the expandable assembly (28) based on the relative location, (III) relate the deflection to contact force applied on expandable assembly (28), and (IV) provide an indication of the contact force on a display (27).

Example 2

The system (10) according to example 1, wherein each of the proximal position sensing element (29) and the at least one distal position sensing element (39) is an electromagnetic coil (EMC).

Example 3

The system (10) according to example 2, wherein a controller (30) is configured to apply a driving signal in a given frequency to one of the proximal EMC and the at least one distal EMC; and receive and process output at the given frequency by the other of the proximal EMC and the at least one distal EMC to determine relative location of each of the at least one distal position sensing element (39) and the proximal position sensing element (29).

Example 4

The system (10) according to example 3, wherein each of the EMCs (29, 39) is configured to sense magnetic fields generated by a magnetic source (32) external to the patient and output respective signals indicative of a position in a 3D coordinate system of a position traction system, and wherein the driving signal has a frequency different from the frequencies used by the magnetic source external to the patient (23).

Example 5

The system (10) according to any one of examples 3-4, and comprising an amplifying circuit fitted on the catheter, the circuit configured to amplify the output at the given frequency by the other of the proximal EMC and the at least one distal EMC.

Example 6

The system (10) according to any one of examples 2-5, wherein the distal end (46) of the shaft (44) includes three EMCs (29) that are non-parallel oriented one with respect to the others, and wherein the processor is configured to detect, by processing the output from the three EMCs, at least one of an axial compression of the expandable assembly (28) and an angular deflection of the expandable assembly (28) relative to the distal end (46) of the shaft (44).

Example 7

The system (10) according to any one of examples 2 through 6, wherein the at least one distal EMC (39) is embedded in a respective electrode disposed (26) on a spline (22).

Example 8

The system (10) according to any of examples 2 through 7, wherein the distal end (46) of the shaft (44) comprises at least two EMCs (29) that are parallel and displaced for one another on the shaft (44).

Example 9

The system (10) according to any one of examples 1 through 8, and comprising a memory (57) configured to store relationship between position sensing elements (29, 39) output and contact force based on empirical data and wherein the processor (56) is configured to use the empirical data to relate position sensing elements output to contact force.

Example 10

The system (10) according to any of examples 1 through 9, wherein the expandable assembly (28) is a basket assembly formed with a plurality of splines (22).

Example 11

A method includes inserting a shaft (44) of a medical probe (14) into a cavity of an organ of a patient (23), the probe comprising (i) an expandable assembly (28) fitted at a distal end (46) of the shaft, wherein the expandable assembly (28) has elastic properties, (ii) a proximal position sensing element (29) mounted on the distal end of the shaft, and (iii) at least one distal position sensing element (39) on a distal end of the expandable assembly (28). Relative location of each of the at least one distal position sensing element (39) and the proximal position sensing element (29) is sensed. Deflection of the expandable assembly (28) is determined based on the relative location. Deflection is related to the contact force applied on the expandable assembly (28). An indication of the contact force is provided on a display (27).

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:
1. A system, comprising:
a medical probe, comprising:
  a shaft for insertion into a cavity of an organ of a patient;
  a proximal position sensing element mounted on the distal end of the shaft;
  an expandable assembly fitted at a distal end of the shaft, the expandable assembly including:
    a cage that is configured to be deformable with elastic properties, the cage configured supporting plurality of electrodes thereon;
    a plurality of electrodes mounted on the cage; and at least one distal position sensing element mounted on a distal end of the cage; and a processor, which is configured to:

sense relative location of each of the at least one distal position sensing element and the proximal position sensing element;

determine deflection of the expandable assembly based on the relative location;

determine contact force applied on the expandable assembly based on the elastic properties of the cage that is pre-defined and deflection of the expandable assembly; and provide an indication of the contact force on a display.

2. The system according to claim 1, wherein each of the proximal position sensing element and the at least one distal position sensing element is an electromagnetic coil (EMC).

3. The system according to claim 2, wherein a controller is configured to:

apply a driving signal in a given frequency to one of the proximal position sensing element and the at least one distal position sensing element; and receive and process output at the given frequency by the other of the proximal position sensing element and the at least one distal position sensing element to determine relative location of each of the at least one distal position sensing element and the proximal position sensing element.

4. The system according to claim 3, wherein each of the proximal position sensing element and the at least one distal position sensing element is configured to sense magnetic fields generated by a magnetic source external to the patient and output respective signals indicative of a position in a 3D coordinate system of a position tracking system, and wherein the driving signal, has a frequency different from frequencies used by the magnetic source external to the patient.

5. The system according claim 3, further comprising an amplifying circuit fitted on the medical probe, the circuit configured to amplify the output at the given frequency by the other of the proximal EMC and the at least one distal EMC.

6. The system according to claim 2, wherein the distal end of the shaft includes three EMCs that are non-parallel oriented one with respect to the others, and wherein the processor is configured to compute at least one of an axial compression of the expandable assembly and an angular deflection of the expandable assembly relative to the distal end of the shaft based on the output from the three EMCS.

7. The system according to claim 2, wherein the at least one distal EMC is embedded in an electrode of the plurality of electrodes.

8. The system according to claim 2, wherein the distal end (46) of the shaft (44) comprises at least two EMCs (29) that are parallel and displaced for one another on the shaft (44).

9. The system according to claim 1, further comprising a memory configured to store relationship between position sensing elements output and contact force based on empirical data and wherein the processor is configured to use the empirical data to relate position sensing elements output to contact force.

10. The system according to claim 1, wherein the cage is a basket formed with a plurality of splines and wherein the plurality of electrodes is mounted on the plurality of splines.

11. A method, comprising:

receiving a first signal from a proximal position sensing element, wherein the proximal position sensing element is mounted on a distal end of a shaft of medical probe;

receiving a second signal from at least one distal position sensing element of an expandable assembly, wherein the expandable assembly includes a cage that is configured to be deformable with elastic properties, a plurality of electrodes mounted on the cage, and the at least one distal position sensing element, the expandable assembly fitted on the distal end of the shaft;

sensing relative location of each of the at least one distal position sensing element and the proximal position sensing element based on the first signal and the second signal;

determining deflection of the expandable assembly based on the relative location;

relating the deflection to the contact force applied on the expandable assembly based on the elastic properties of the cage; and providing an indication of the contact force on a display.

12. The method according to claim 11, wherein each of the proximal position sensing element and the at least one distal position sensing element is an electromagnetic coil (EMC).

13. The method according to claim 12, further comprising:

applying a driving signal in a given frequency to one of the proximal position sensing element and the at least one distal position sensing element; and receiving and processing output at the given frequency by the other of the proximal position sensing element and the at least one distal position sensing element to determine relative location of each of the at least one distal position sensing element and the proximal position sensing element.

14. The method according to claim 13, wherein each of the proximal position sensing element and the at least one distal position sensing element is configured to sense magnetic fields generated by a magnetic source external to the patient and output respective signals indicative of a position in a 3D coordinate system of a position tracking system, and wherein the driving signal has a frequency different from frequencies used by the magnetic source external to the patient.

15. The method according to claim 13, further comprising amplifying the output from the at least one distal position sensing element using an amplifying circuit fitted on the medical probe.

16. The method according to claim 12, wherein the distal end of the shaft includes three EMCs that are non-parallel oriented one with respect to the others, and wherein the method further comprises computing at least one of an axial compression of the expandable assembly and an angular deflection of the expandable assembly relative to the distal end of the shaft based on the output from the three EMCs.

17. The method according to claim 12, wherein the at least one distal EMC is embedded in an electrode of the plurality of electrodes.

18. The method according to claim 12, further comprising storing relationship between EMCs output and contact force based on empirical data and using the empirical data to relate EMCs output to contact force.

19. The method according to claim 12, wherein the cage is a basket formed with a plurality of splines.

\* \* \* \* \*